(12) United States Patent
Kovacs et al.

(10) Patent No.: US 10,258,478 B2
(45) Date of Patent: Apr. 16, 2019

(54) GLENOID IMPLANT

(71) Applicant: Biomet Manufacturing, LLC, Warsaw, IN (US)

(72) Inventors: Michael Francis Kovacs, Warsaw, IN (US); John M. McDaniel, Warsaw, IN (US); Nathan A. Winslow, Warsaw, IN (US); Thomas M. Vanasse, Gainesville, FL (US); Michael A. Wack, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/815,462

(22) Filed: Nov. 16, 2017

(65) Prior Publication Data

US 2018/0071104 A1 Mar. 15, 2018

Related U.S. Application Data

(62) Division of application No. 14/459,935, filed on Aug. 14, 2014, now Pat. No. 9,844,440.

(51) Int. Cl.
*A61F 2/40* (2006.01)
*A61F 2/30* (2006.01)

(52) U.S. Cl.
CPC ........ *A61F 2/4081* (2013.01); *A61F 2/30734* (2013.01); *A61F 2/30749* (2013.01); *A61F 2002/3038* (2013.01); *A61F 2002/30242* (2013.01); *A61F 2002/30369* (2013.01); *A61F 2002/30736* (2013.01); *A61F 2002/30825* (2013.01); *A61F 2002/30841* (2013.01); *A61F 2002/30878* (2013.01); *A61F 2002/30879* (2013.01); *A61F 2002/30881* (2013.01); *A61F 2002/30891* (2013.01)

(58) Field of Classification Search
CPC .................. A61F 2/4081; A61F 2002/3038
See application file for complete search history.

(56) References Cited

U.S. PATENT DOCUMENTS

| 5,800,551 A | 9/1998 | Williamson et al. |
| 6,699,289 B2 | 3/2004 | Iannotti et al. |
| (Continued) | | |

FOREIGN PATENT DOCUMENTS

| CN | 101340862 A | 1/2009 |
| CN | 103108612 A | 5/2013 |
| (Continued) | | |

OTHER PUBLICATIONS

"European Application Serial No. 15750604.9, Response filed Oct. 10, 2017 to Office Action dated Mar. 31, 2017", 11pgs.

(Continued)

*Primary Examiner* — Brian Dukert
(74) *Attorney, Agent, or Firm* — Schwegman Lundberg & Woessner, P.A.

(57) ABSTRACT

A glenoid implant is provided and may include a body portion and a stem portion. The stem portion may extend from the body portion along a longitudinal axis. The body portion may include an articular side and a bone-engaging side opposite the articular side. At least a portion of the bone-engaging side may be disposed at a non-parallel angle relative to at least a peripheral edge of the articulation side.

17 Claims, 11 Drawing Sheets

(56) References Cited

U.S. PATENT DOCUMENTS

| | | | |
|---|---|---|---|
| 8,080,063 B2* | 12/2011 | Ferrand | A61F 2/4081 623/19.11 |
| 8,556,980 B2 | 10/2013 | Deffenbaugh | |
| 9,844,440 B2 | 12/2017 | Kovacs et al. | |
| 2003/0114933 A1 | 6/2003 | Bouttens et al. | |
| 2005/0261775 A1 | 11/2005 | Baum et al. | |
| 2006/0069444 A1 | 3/2006 | Deffenbaugh | |
| 2009/0125113 A1 | 5/2009 | Guederian et al. | |
| 2010/0161066 A1 | 6/2010 | Iannotti et al. | |
| 2010/0217399 A1 | 8/2010 | Groh | |
| 2010/0228352 A1 | 9/2010 | Courtney, Jr. et al. | |
| 2010/0241235 A1* | 9/2010 | Basamania | A61F 2/4081 623/19.11 |
| 2011/0035013 A1* | 2/2011 | Winslow | A61F 2/4003 623/19.13 |
| 2015/0374502 A1 | 12/2015 | Hodorek et al. | |
| 2016/0045323 A1 | 2/2016 | Kovacs et al. | |

FOREIGN PATENT DOCUMENTS

| | | | |
|---|---|---|---|
| CN | 103491906 A | 1/2014 | |
| CN | 103702627 A | 4/2014 | |
| CN | 107072791 A | 8/2017 | |
| EP | 0339530 A2 | 11/1989 | |
| EP | 1598034 A1 | 11/2005 | |
| EP | 2057970 A2 | 5/2009 | |
| EP | 2201912 A1 | 6/2010 | |
| EP | 2749255 A1 * | 7/2014 | A61F 2/40 |
| FR | 2704747 A1 | 11/1994 | |
| FR | 2780635 A1 | 1/2000 | |
| JP | 2017523872 A | 8/2017 | |
| WO | WO-2016025378 A1 | 2/2016 | |

OTHER PUBLICATIONS

"U.S. Appl. No. 14/459,935, Advisory Action dated Jul. 6, 2017", 3 pgs.
"U.S. Appl. No. 14/459,935, Advisory Action dated Nov. 1, 2016", 3 pgs.
"U.S. Appl. No. 14/459,935, Final Office Action dated May 10, 2017", 10 pgs.
"U.S. Appl. No. 14/459,935, Final Office Action dated Aug. 30, 2016", 11 pgs.
"U.S. Appl. No. 14/459,935, Non Final Office Action dated Jan. 31, 2017", 10 pgs.
"U.S. Appl. No. 14/459,935, Non Final Office Action dated Mar. 9, 2016", 10 pgs.
"U.S. Appl. No. 14/459,935, Notice of Allowance dated Aug. 17, 2017", 5 pgs.
"U.S. Appl. No. 14/459,935, Response filed Jan. 25, 2016 to Restriction Requirement dated Dec. 4, 2015", 6 pgs.
"U.S. Appl. No. 14/459,935, Response filed Mar. 22, 2017 to Non Final Office Action dated Jan. 31, 2017", 11 pgs.
"U.S. Appl. No. 14/459,935, Response filed Jun. 9, 2016 to Non Final Office Action dated Mar. 9, 2016", 10 pgs.
"U.S. Appl. No. 14/459,935, Response filed Jun. 23, 2017 to Final Office Action dated May 10, 2017", 12 pgs.
"U.S. Appl. No. 14/459,935, Response filed Oct. 24, 2016 to Final Office Action dated Aug. 30, 2016", 15 pgs.
"U.S. Appl. No. 14/459,935, Restriction Requirement dated Dec. 4, 2015", 6 pgs.
"U.S. Appl. No. PCT/US2015/044448, Invitation to Pay Add'l Fees and Partial Search Rpt dated Oct. 15, 2015", 23 pgs.
"Comprehensive® Total Shoulder System Featuring Comprehensive® Access Glenoid Instrumentation Surgical Technique", Biomet® Orthopedics, (2012), 1-56.
"Exactech Shoulder Operative Technique; Equinoxe Platform Shoulder System", Exactech 718-01-30 Rev. D, Equinoxe Primary/ Reverse Op Tech 0413, (Jan 2013), 60 pgs.
"Global® Steptech® Anchor Peg Glenoid Surgical Technique", DePuy Synthes Joint Reconstruction, (2014), 1-32.
"International Application Serial No. PCT/US2015/044448, International Preliminary Report on Patentability dated Feb. 23, 2017", 12 pgs.
"International Application Serial No. PCT/US2015/044448, International Search Report dated Dec. 31, 2015", 7 pgs.
"International Application Serial No. PCT/US2015/044448, Written Opinion dated Dec. 31, 2015", 10 pgs.
Neer, Charles S., et al., "Glenoid Bone-Grafting in Total Shoulder Arthroplasty", The Journal of Bone and Joint Surgery, vol. 70-A, No. 8,, (Sep. 1998), pp. 1154-1162.
"Australian Application Serial No. 2015302017, Response filed Jun. 21, 2018 to First Examination Report dated May 23, 2018", 1 pg.
"Chinese Application Serial No. 201580050317.9, Response filed Aug. 3, 2018 to Office Action dated May 3, 2018", (W/ English claims), 11 pgs.
"Japanese Application Serial No. 2017-508061, Office Action dated Jun. 26, 2018", W/English Translation, 11 pgs.
"Australian Application Serial No. 2015302017, First Examination Report dated May 23, 2018", 2 pgs.
"Chinese Application Serial No. 201580050317.9, Office Action dated May 3, 2018", (W/ English Translation), 21 pgs.
"Japanese Application Serial No. 2017-508061, Response filed Sep. 26, 2018 to Office Action dated Jun. 26, 2018", w English claims, 22 pgs.
"Chinese Application Serial No. 201580050317.9, Office Action dated Nov. 13, 2018", w English Translation, 5 pgs.

* cited by examiner

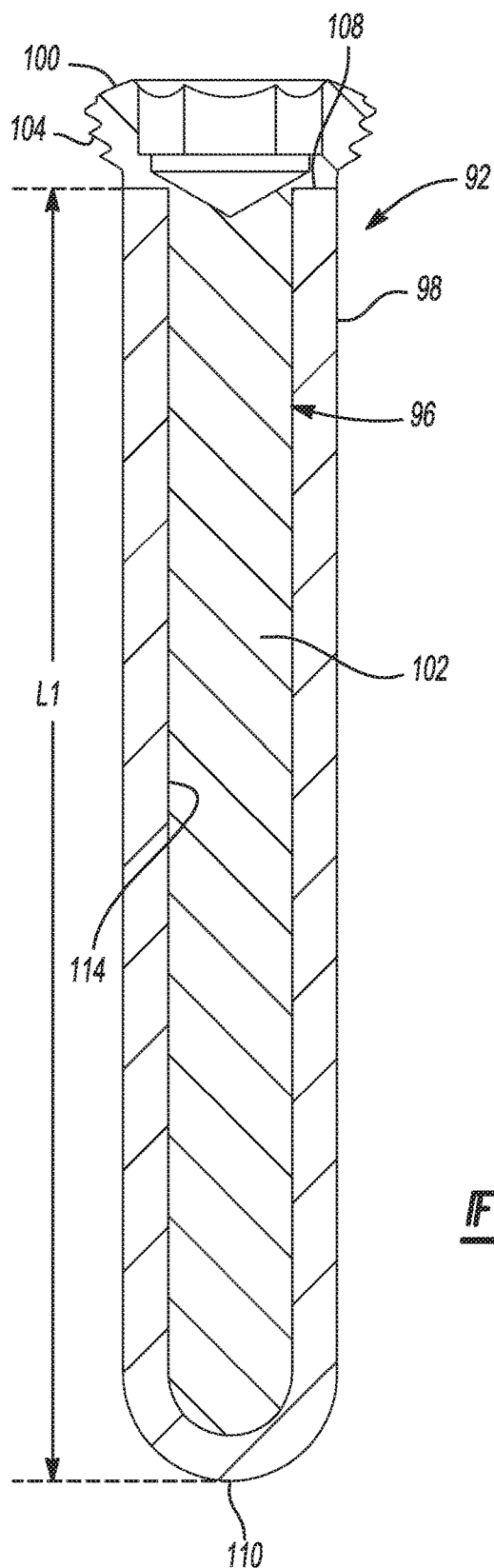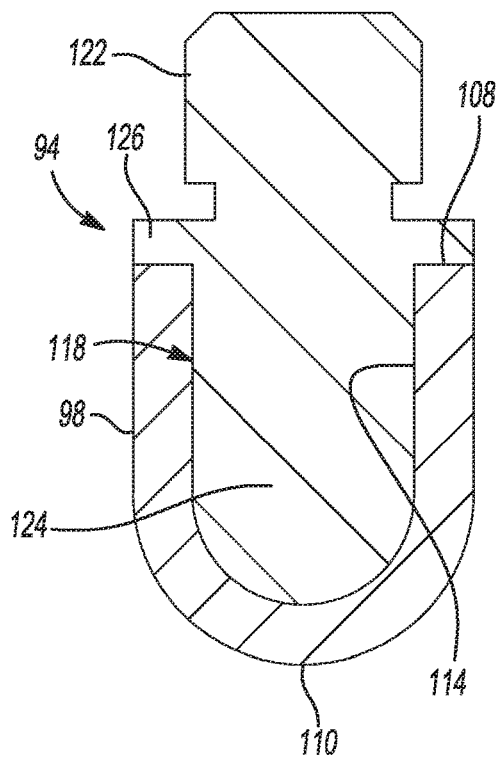
Fig-10B
Fig-10A

GLENOID IMPLANT

CLAIM OF PRIORITY

This application is a Divisional of U.S. patent application Ser. No. 14/459,935, filed on Aug. 14, 2014, which is incorporated herein by reference in its entirety.

FIELD

The present disclosure relates to a surgical implant, and more particularly to a glenoid implant having an angled bone-engaging portion or surface.

BACKGROUND

This section provides background information related to the present disclosure which is not necessarily prior art.

Surgical procedures for repairing or reconstructing a joint may require securely fastening a surgical implant to a bone. For example, shoulder joint procedures, such as reverse and/or anatomic shoulder arthroplasty, may require fixing a glenoid implant to a scapula to reproduce or replicate a glenoid cavity on the scapula. In such procedures, it is desirable to ensure the accurate placement and alignment of the implant relative to the glenoid. To ensure the accurate placement and alignment of the implant relative to the glenoid, often a total shoulder arthroplasty procedure will involve fixing a bone graft to the glenoid and/or reaming the glenoid in order to account for bone deficiencies and erosion of the glenoid. Fixing a bone graft to the glenoid and/or reaming the glenoid can help to return the glenoid surface to its natural position and profile, and thus ensure the accurate and secure placement of the implant relative to the glenoid.

While known surgical procedures and surgical implants have proven to be acceptable for their intended purposes, a continuous need for improvement in the relevant arts remains.

SUMMARY

This section provides a general summary of the disclosure, and is not a comprehensive disclosure of its full scope or all of its features.

According to one particular aspect, the present disclosure provides a glenoid implant. The glenoid implant may include a body portion and a stem portion. The stem portion may extend from the body portion along a longitudinal axis. The body portion may include an articular side and a bone-engaging side opposite the articular side. At least a portion of the bone-engaging side may be disposed at a non-parallel angle relative to at least a peripheral edge of the articulation side.

In some configurations, the bone-engaging side may include a substantially spherical bone-engaging surface.

In some configurations, the bone-engaging surface may include a first portion and a second portion. The first portion may be disposed at a first angle $\alpha 1$ relative to at least the peripheral edge of the articular side, and the second portion may be disposed at a second, different angle $\alpha 2$ relative to at least the peripheral edge.

In some configurations, the first portion may extend about the longitudinal axis by an angle $\theta$.

In some configurations, the angle $\theta$ may be substantially equal to 180°.

In some configurations, the bone-engaging surface may include an array of teeth extending therefrom.

In some configurations, the articular side may be configured to partially receive a humeral head.

In some configurations, the articular side may be configured to receive a glenosphere.

In some configurations, the articular side may at least partially define a concave hemispherical shape.

In some configurations, the bone-engaging side may include a plurality of blades. Each blade of the plurality of blades may include a proximal end, a distal end, an inner side and an outer side. The proximal end may be adjacent to the bone-engaging side. The distal end may define a wedge-shaped construct with at least a portion of the articular side.

In some configurations, the inner side and the stem portion may define a radially extending void therebetween.

In some configurations, the distal ends of the plurality of blades may collectively define a substantially spherical profile.

In some configurations, each of the plurality of blades may define a length X extending between the proximal end and the distal end. A length X1 of a first blade may be less than a length X2 of a second blade.

In some configurations, the length L may vary between the inner side and the outer side.

In some configurations, the bone-engaging side may include a plurality of fixation members.

In some configurations, the fixation member may include a first annular fin and a second annular fin. The fixation member may define an annular groove disposed between the first annular fin and the second annular fin.

In some configurations, the glenoid implant may include a plurality of peg assemblies. Each peg assembly may have a length L extending from a proximal end to a distal end. The proximal end may be coupled to the body portion.

In some configurations, a length L1 of a first peg assembly may be less than a length L2 of a second peg assembly.

In some configurations, the articular side and the distal ends of the plurality of peg assemblies may define a wedge-shaped construct.

According to another particular aspect, the present disclosure provides a glenoid implant. The glenoid implant may include a stem portion and a body portion. The stem portion may have a longitudinal axis. The body portion may be carried at a distal end of the stem portion. The body portion may include an articular side, a bone-engaging side opposite the articular side, and a peripheral sidewall extending between the articular side and the bone-engaging side. The peripheral sidewall may have a depth parallel to the longitudinal axis. At least a portion of the peripheral sidewall may increase in depth in a direction perpendicular to the longitudinal axis.

According to yet another particular aspect, the present disclosure provides a glenoid implant. The glenoid implant may include a body portion, a first insert and a second insert. The body portion may include an articular side, a bone-engaging side opposite the articular side, a first aperture, and a second aperture. The first and second apertures may extend between the articular and bone-engaging sides. The second aperture may have an elongate shape. The first insert may be coupled to the body portion, and may include a first peg portion disposed in the first aperture. The second insert may be rotatably coupled to the body portion and may include a second peg portion disposed in the second aperture.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 10A is a cross-sectional view of the first peg assembly of FIG. 9A;

FIG. 10B is a cross-sectional view of the second peg assembly of FIG. 9A;

Corresponding reference numerals indicate corresponding parts throughout the several views of the drawings.

DETAILED DESCRIPTION

Figure 1:
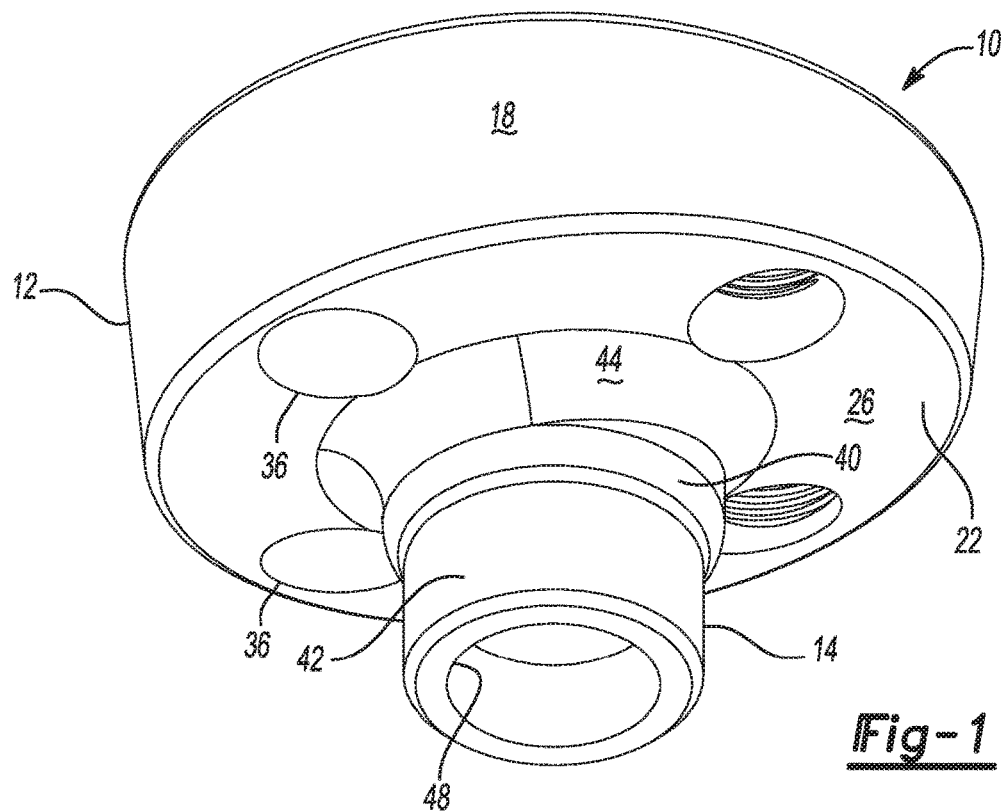
FIG. 1 is a perspective view of a glenoid implant constructed in accordance with the principles of the present disclosure.

Example embodiments will now be described more fully with reference to the accompanying drawings.

With initial reference to FIGS. 1, 2A, 3A and 4, an implant constructed in accordance with the principles of the present disclosure is illustrated and generally identified at reference character 10. According to one exemplary use, the implant 10 may be a glenoid implant for use in shoulder joint replacement. In such case, the glenoid implant can replace or replicate an entire glenoid cavity (not shown) or a portion thereof for anatomic shoulder joint replacements. The glenoid implant can also fill a defect in the glenoid cavity such as a void due to severe wear. It will also be appreciated, however, that the present teachings may be adapted to fix various implants to various bones.

The implant 10 may include a body portion 12 and a central fixation member or stem 14. While the implant 10 is generally shown and described herein as being monolithic, or an otherwise integrally formed construct, it will be appreciated that the body portion 12 and stem 14 may be formed as separate components and thereafter mechanically joined, press-fit, or threaded into an aperture formed in the body 12, such that the stem 14 extends from the body portion 12 along a longitudinal axis 16.

The implant 10 can be formed from any biocompatible material, including, polymer, ceramic, metal or combinations thereof, and can be formed using any suitable manufacturing technique, including machining, direct compression molding and/or additive manufacturing which enables forming multiple implants in a single build and decreases manufacturing time. Once formed, the implant 10 can be further processed (e.g., polished, blasted, machining) as desired. For example, the implant 10 can be polished for articulation with a humeral head made from polyethylene or another suitable material. Alternatively, polyethylene can be molded over or pressed onto the body 12 for articulation with a metal humeral head.

The body 12 may include a peripheral surface 18, an articular surface or side 20, and a bone-engaging surface or side 22 opposite from the articular side 20. As illustrated, in one configuration, the peripheral surface 18 may define a generally circular or cylindrically shaped body 12. It will also be appreciated that the peripheral surface 18 may define other shapes (e.g., rectangular, oval, pear-shaped, etc.) within the scope of the present disclosure. In this regard, the peripheral surface 18 can be patient-specific and can match or replicate a peripheral surface of a glenoid cavity of a specific patient.

Figure 2A:
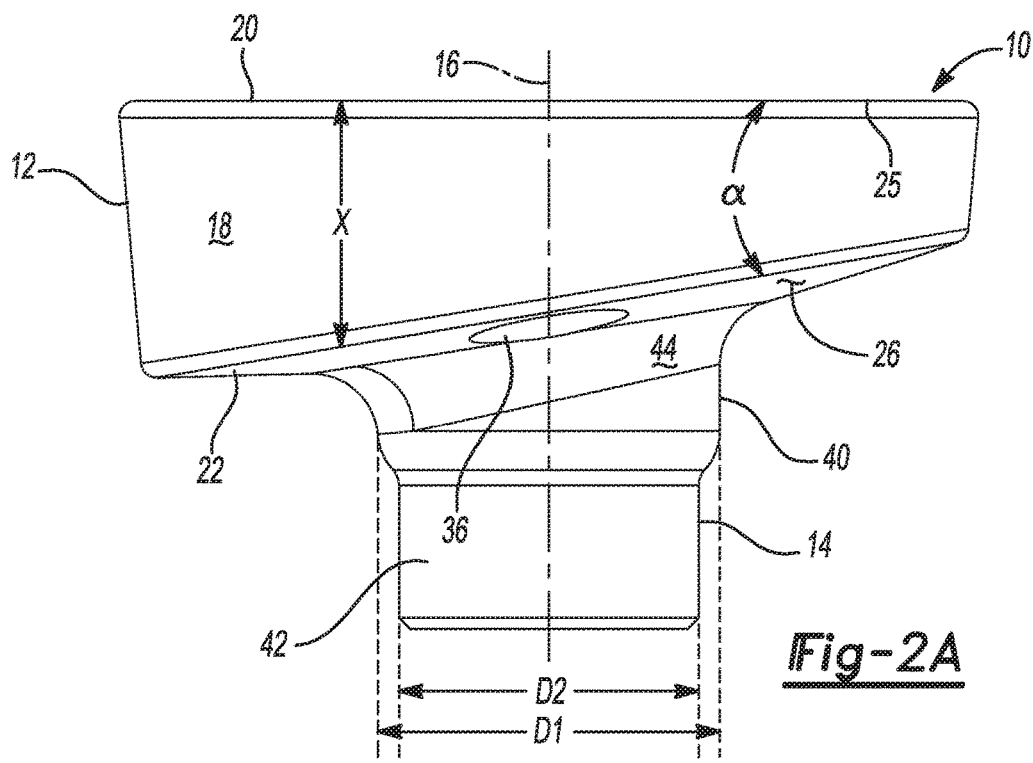
FIG. 2A is a side view of the glenoid implant of FIG. 1.

The articular side 20 of the implant 10 may be configured to partially receive and nestingly engage or articulate with the head of a humerus (not shown). For example, the articular side 20 can include a concave hemispherically shaped surface that closely conforms as a mirror-image of a complementary surface of the humeral head. In this regard, as illustrated in FIG. 2A, an outer peripheral edge 25 of the articular side 20 may define a plane that is substantially perpendicular to the longitudinal axis 16. The humeral head can be part of the natural humerus of a specific patient, or the humeral head can be part of a humeral implant. In other configurations, the articular side 20 of the implant 10 may be configured to receive a glenosphere 23 (e.g., FIG. 9A), including a stem portion 24 thereof.

The bone-engaging side 22 may be configured to nestingly engage with the glenoid cavity, or other bone surface. The bone-engaging side 22 may include a surface 26. In some configurations, the surface 26 may be convex, defining a substantially spherical profile. As illustrated in FIG. 2A, the surface 26 may be sloped such that the surface 26 further defines an angle α with the outer peripheral edge 25 of the articular side 20. In certain embodiments, the angle α may be between zero degrees (0°) and thirty degrees (30°), such that the surface 26 and the articular side 20 may define a substantially wedge-shaped construct. In this regard, a depth or distance X, extending in a direction substantially parallel to the longitudinal axis 16, between the surface 26 and the outer peripheral edge 25 of the articular side 20 (i.e., a depth of the peripheral surface 18) may vary.

A plurality of apertures 36 may extend through the body 12, between the articular side 20 and the bone-engaging side 22. As illustrated, in one configuration the implant 10 may include four equally sized and spaced apertures 36. It will be appreciated, however, that the implant 10 may include more or less than four apertures 36 within the scope of the present disclosure. The apertures 36 may extend through the body 12 along axes 39, and may be sized and shaped to receive mechanical fasteners (e.g., bone screws 38) for fixing the implant 10 to the bone. The axes 39 may form an angle β with the longitudinal axis 16. It will also be appreciated that the implant 10 may be configured to be fixed to the bone without using bone screws 38. In this regard, the implant 10 may be configured such that the stem 14 can be press-fit into holes formed in the bone in order to fix the implant 10 to the bone. In addition, the implant 10 may be configured to receive bone cement on the stem 14 to fix the stem 14 within a corresponding bore or hole in the bone.

The stem 14 may include a proximal end or portion 40 and a distal end or portion 42. The proximal portion 40 may extend from the bone-engaging side 22 of the body 12 along the longitudinal axis 16. In this regard, the stem 14 may be centrally located relative to the bone-engaging side 22. In one configuration, the proximal portion 40 may be substantially cylindrical, defining a diameter D1. The proximal portion 40 may include a tapered or concavely radiused surface 44 adjacent the bone-engaging side 22, and a convexly radiused surface 46 adjacent the distal portion 42. In one configuration, the distal portion 42 may be substantially cylindrical, defining a diameter D2 that is less than the diameter D1. The distal portion 42 may extend from the proximal portion 40 along the longitudinal axis 16, such that the distal portion 42 is concentrically formed relative to the proximal portion 40.

An aperture 48 may extend through the stem 14 and the body 12 along the longitudinal axis 16. The aperture 48 may be sized and shaped to receive an insert or removable fastener (not shown). The insert and/or a peripheral surface of the aperture 48 may be coated with a porous material for improving the in-growth of bone into the aperture 48, and thus improve the stability and fixation of the implant 10 relative to the bone by ensuring a secure connection between the stem 14 and a corresponding hole in the bone. Similarly, the bone-engaging surface 22 may be coated with a porous material for improving the in-growth of bone into the aperture 48 and/or the apertures 36.

Figure 2B:
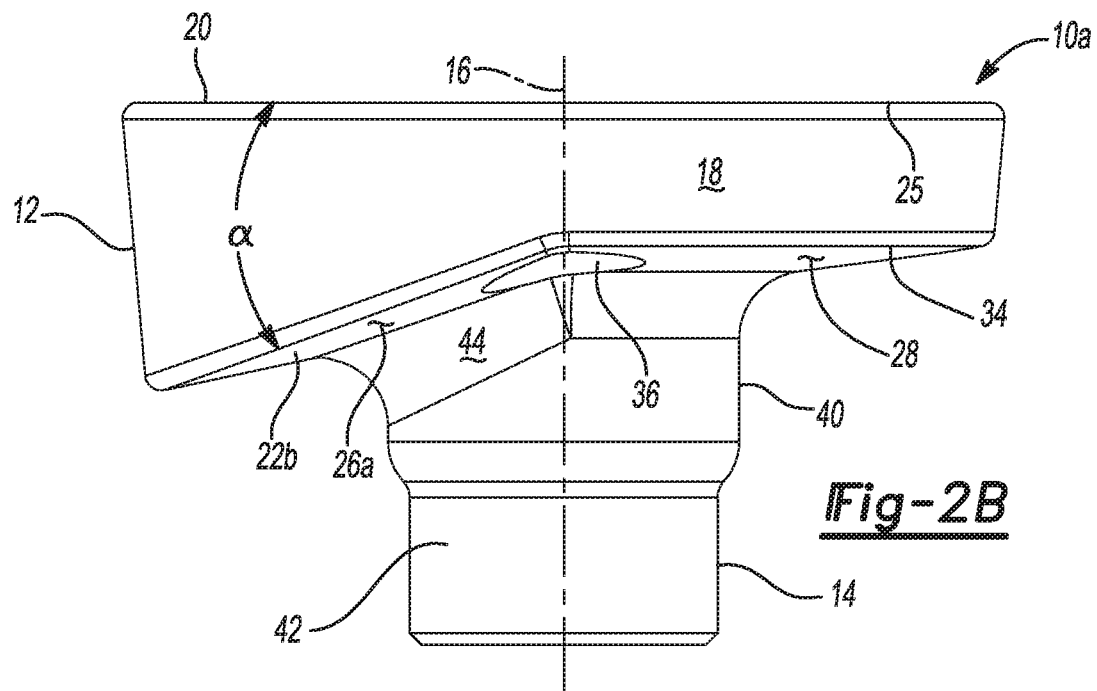
FIG. 2B is a side view of another glenoid implant constructed in accordance with the principles of the present disclosure.
Figure 3A:
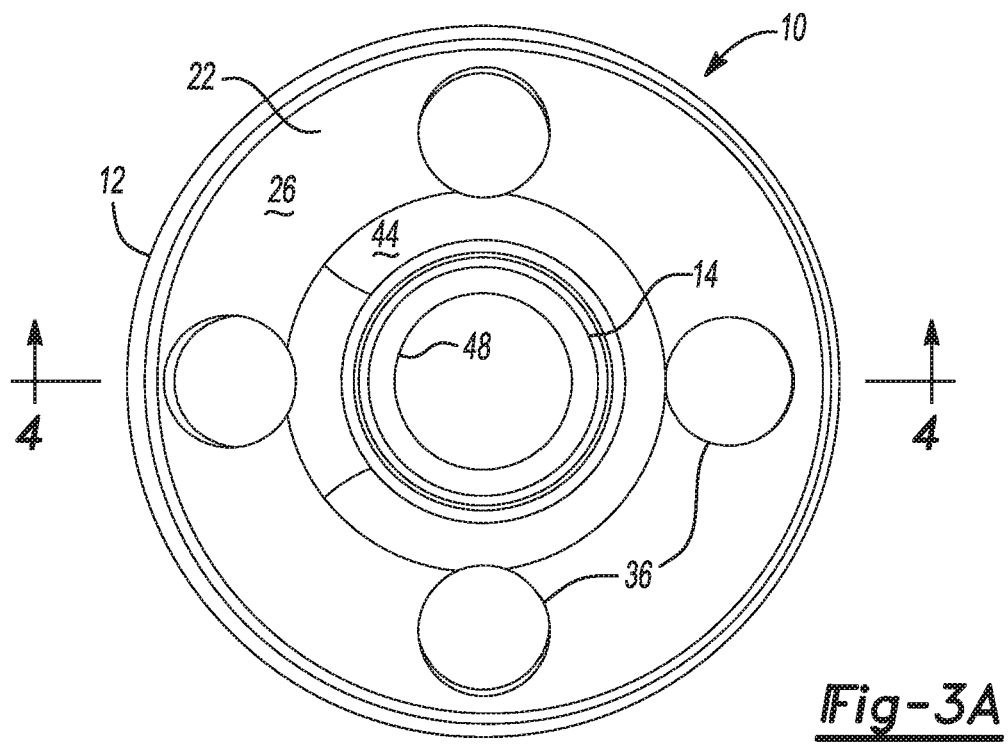
FIG. 3A is a bottom view of the glenoid implant of FIG. 1.
Figure 3B:
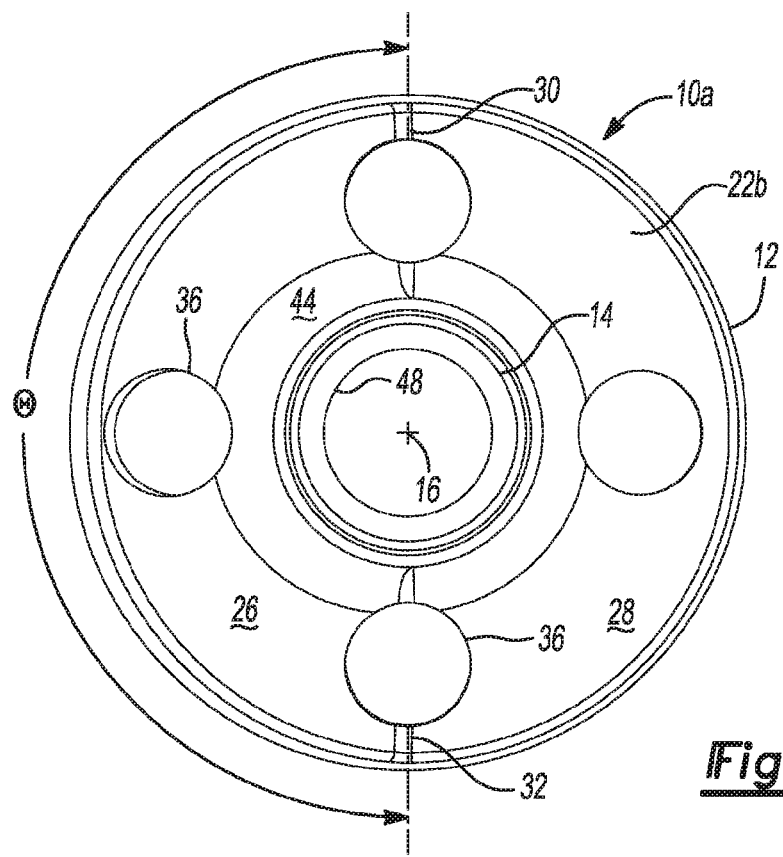
FIG. 3B is a bottom view of the glenoid implant of FIG. 2B.
Figure 4:
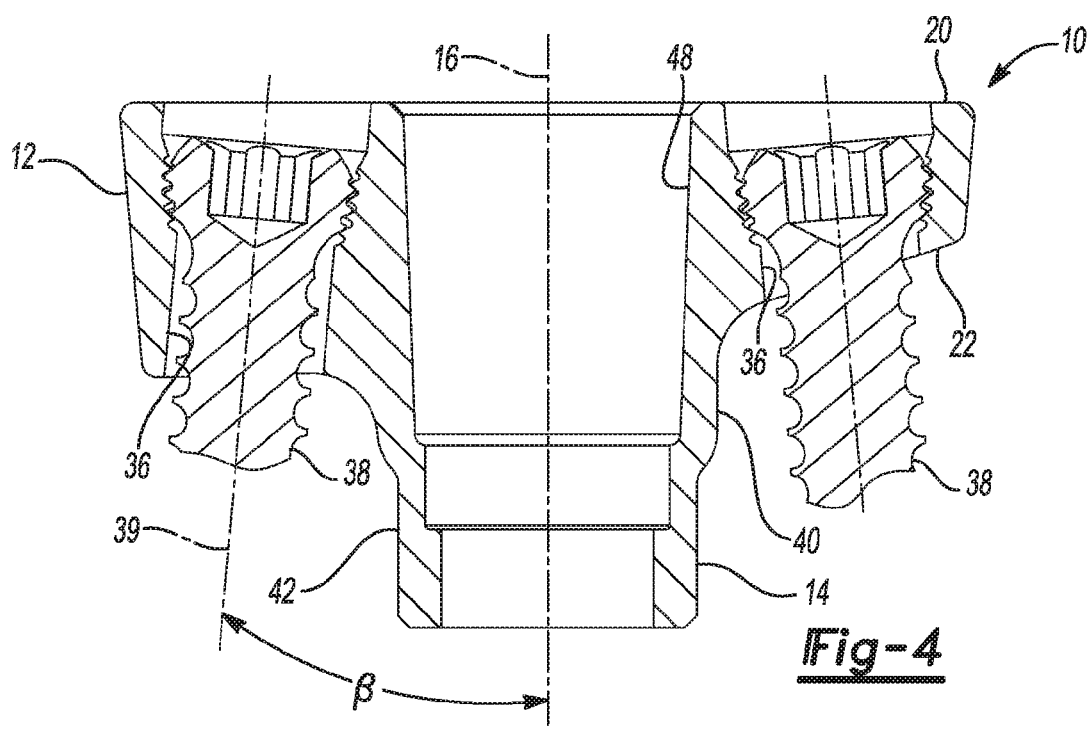
FIG. 4 is a cross-sectional view of the glenoid implant of FIG. 3A, taken through the line 4-4.

With reference to FIGS. 2B and 3B, another configuration of an implant is shown and generally identified at reference character 10a. The implant 10a may be substantially similar to the implant 10, except as otherwise provided herein. Accordingly, like reference numerals are used hereinafter and in the drawings to identify like components, while like reference numerals containing letter extensions (i.e., "a") are used to identify those components that have been modified.

A bone-engaging side 22a of the implant 10a may be at least partially defined by a first portion or surface 26a and a second portion or surface 28. As illustrated in FIG. 3B, the first and second surfaces 26a, 28 may extend between first and second ends 30, 32, such that the first surface 26a extends about the longitudinal axis 16 from the first end 30 to the second end 32, and the second surface 28 extends about the longitudinal axis 16 from the second end 32 to the first end 30. In this regard, the first surface 26a may extend about the longitudinal axis 16 by an angle θ. In one configuration, the angle θ may be substantially equal to one hundred eighty degrees (180°). It will be appreciated, however, that the angle θ may be greater or less than one hundred eighty degrees (180°) within the scope of the present disclosure. As will be explained in more detail below, the angles θ and α may allow the surgeon to uniquely customize the implant 10a for a particular patient.

In some configurations, the first surface 26a may be convex, defining a substantially spherical profile. The first surface 26a may further define the angle α with the outer peripheral edge 25 of the articular side 20, such that the first surface 26a and the articular side 20 define a substantially wedge-shaped construct. The second surface 28 may be substantially planar, or slightly convex. In this regard, the second surface 28 may include an outer peripheral edge 34 that is substantially parallel to the outer peripheral edge 25 of the articular side 20 (i.e., disposed at an angle of approximately zero degrees (0°) relative to the outer peripheral edge 25), and substantially perpendicular to the longitudinal axis 16.

An example method of repairing a bone, such as a glenoid cavity of a scapula (not shown), will now be described. First, a surgeon may drill or otherwise form at least one hole in the glenoid cavity. A first hole can be sized for receiving the stem 14. A plurality of second holes can be sized for receiving the bone screws 38. A surface of the scapula can be reamed, or otherwise resurfaced, to remove an eroded portion of the bone. The implant 10 may be placed within the glenoid cavity such that the surface 26 engages the bone. The implant 10 may be rotated about the longitudinal axis 16, before or after the surface 26 is engaged with the bone, such that the angle α allows the outer peripheral edge 25 of the articular side 20 to be substantially aligned, or otherwise flush with, the surface of the bone. In this position, the apertures 36 may be aligned with the second holes.

It will be appreciated that the configuration of the implant 10, including the configuration of the surfaces 26, 26a, and 28, can allow for the use of a single implant 10, 10a in multiple positions and configurations relative to the bone, while also minimizing the need for excessive reaming and/or the use of bone grafts to account for erosion in an implant-engaging surface of the bone.

Figure 5:
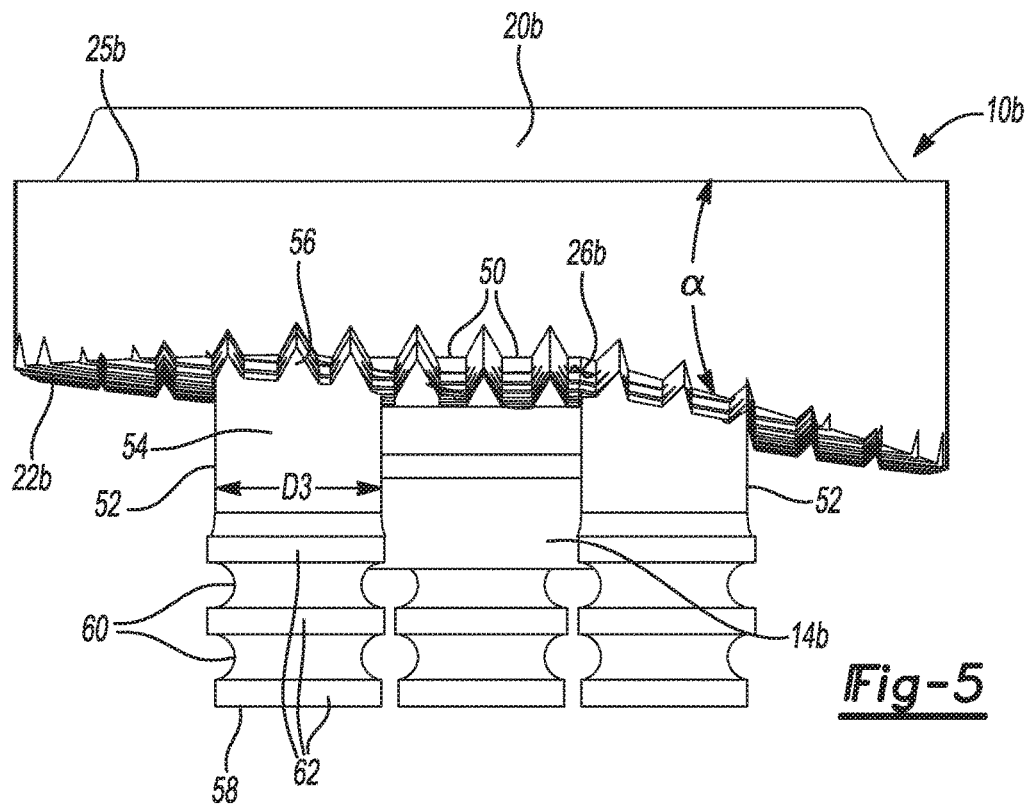
FIG. 5 is a side view of another glenoid implant constructed in accordance with the principles of the present disclosure.

With reference to FIG. 5, another implant constructed in accordance with the present teachings is illustrated and generally identified at reference character 10b. The structure and function of the implant 10b may be similar or identical to the structure and function of the implant 10 described above, apart from any exceptions described below and/or shown in the figures. Accordingly, similar features will not be described again in detail. Like reference numerals are used hereinafter and in the drawings to identify like components, while like reference numerals containing letter extensions (i.e., "b") are used to identify those components that have been modified.

The implant 10b may be used in an anatomic shoulder arthroplasty procedure. Accordingly, the bone-engaging side 22b of the implant 10b may include a plurality of protrusions or teeth 50 and a plurality of peripheral fixation members or pegs 52 extending therefrom. The teeth 50 may be shaped as pyramidal frustums. In one configuration, the teeth 50 may be shaped as truncated square pyramids. The teeth 50 may be arranged in a grid or array of orthogonally disposed rows, helping bone cement to flow or otherwise disburse between the bone and the bone-engaging side.

The peripheral pegs 52 may include a substantially cylindrical body 54 extending between a proximal end 56 and a distal end 58 and having a diameter D3. The proximal end 56 may be adjacent to the bone-engaging side 22b of the body 54. The peripheral pegs 52 may also include an annular groove 60 formed in a peripheral surface of the body 54. As illustrated, in one configuration, each peripheral peg 52 includes two annular grooves 60 defining three annular fin portions 62 of the body 54. It will be appreciated, however, that each peg 52 may include more or less than three annular grooves 60 and fin portions 62 within the scope of the present disclosure. In this regard, a further discussion of the peripheral pegs 52, including various configurations and functions thereof, may be found in commonly owned U.S. patent application Ser. No. 14/226,051 filed Mar. 26, 2014 and entitled "Press-Fit Glenoid With Peripheral Compression Pegs", which is hereby incorporated by reference in its entirety.

An example method of repairing a scapula with the implant 10b may include drilling or otherwise forming a plurality of holes in the scapula. A first hole can be sized for receiving the stem 14. A plurality of second holes can be sized for receiving the peripheral pegs 52. A surface of the scapula can be reamed, or otherwise resurfaced, to remove an eroded portion of the bone. The implant 10b may be placed within the glenoid cavity such that the first surface 26b of the bone-engaging side 22b is substantially aligned with the reamed or resurfaced portion of the bone, and the peripheral pegs 52 are substantially aligned with the plurality of second holes. In this regard, the implant 10b may be rotated about the longitudinal axis 16, before the first surface 26b is engaged with the bone, such that the angle α formed by the first surface 26b allows the outer peripheral edge 25b of the articular side 20b to be substantially aligned, or otherwise flush with, the surface of the bone.

A force may be applied to the implant 10b such that the annular fin portions 62 engage the second holes of the scapula in a press-fit configuration. In this regard, it will be appreciated that the fin portions 62 may deform or otherwise flex to ensure stability and a secure fit between the implant 10b and the scapula. Bone cement may be inserted into the second holes in the scapula. The bone cement may flow into the annular grooves 60 to ensure that the implant 10b is adequately secured to the scapula.

Figure 6:
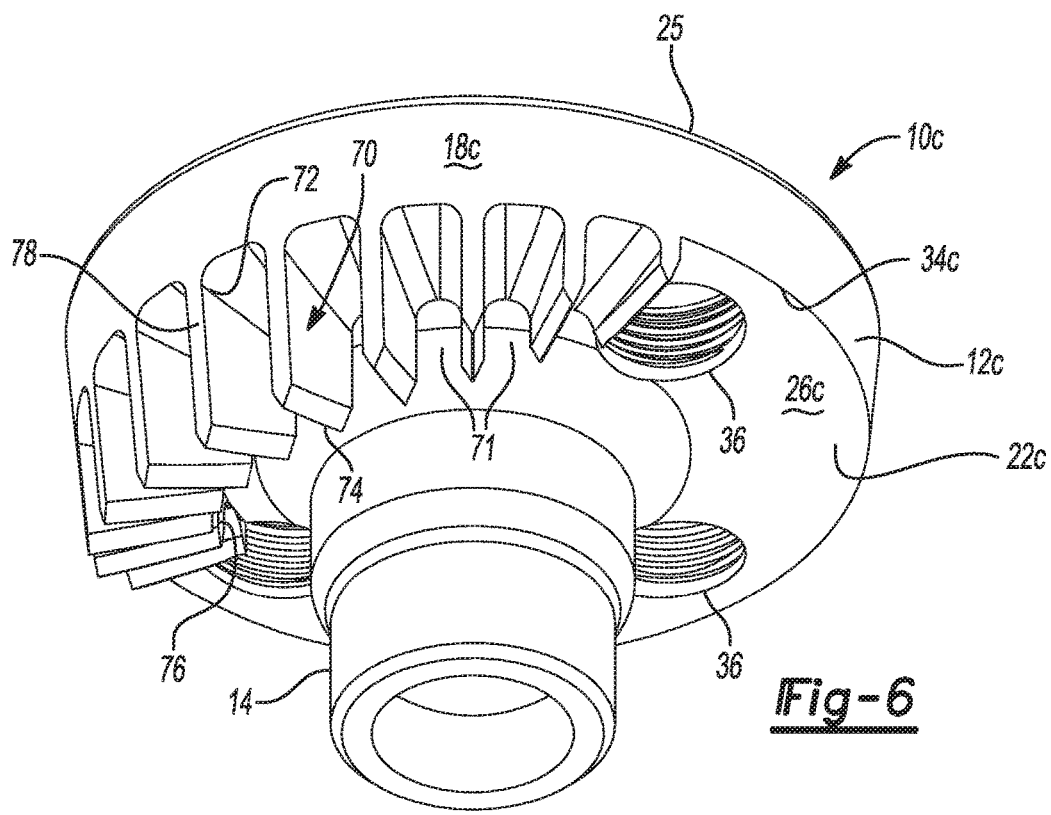
FIG. 6 is a perspective view of another glenoid implant constructed in accordance with the principles of the present disclosure.
Figure 7:
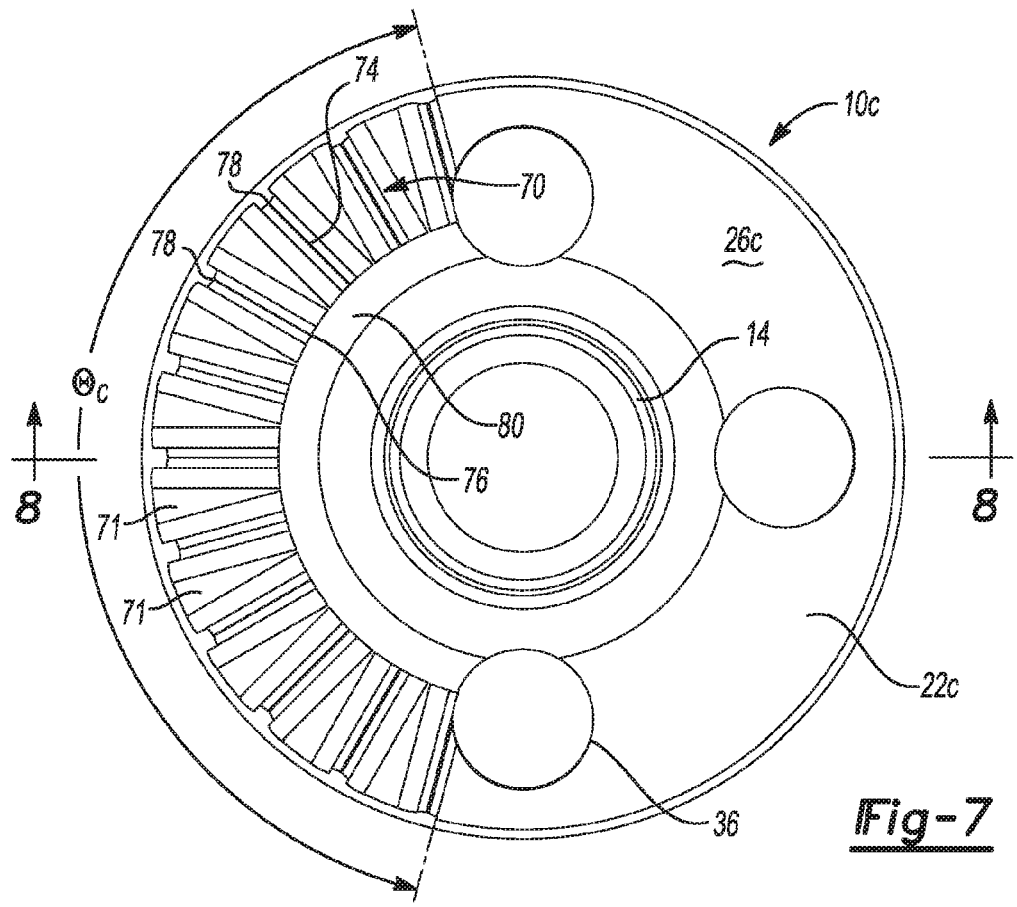
FIG. 7 is a bottom view of the glenoid implant of FIG. 6.
Figure 8:
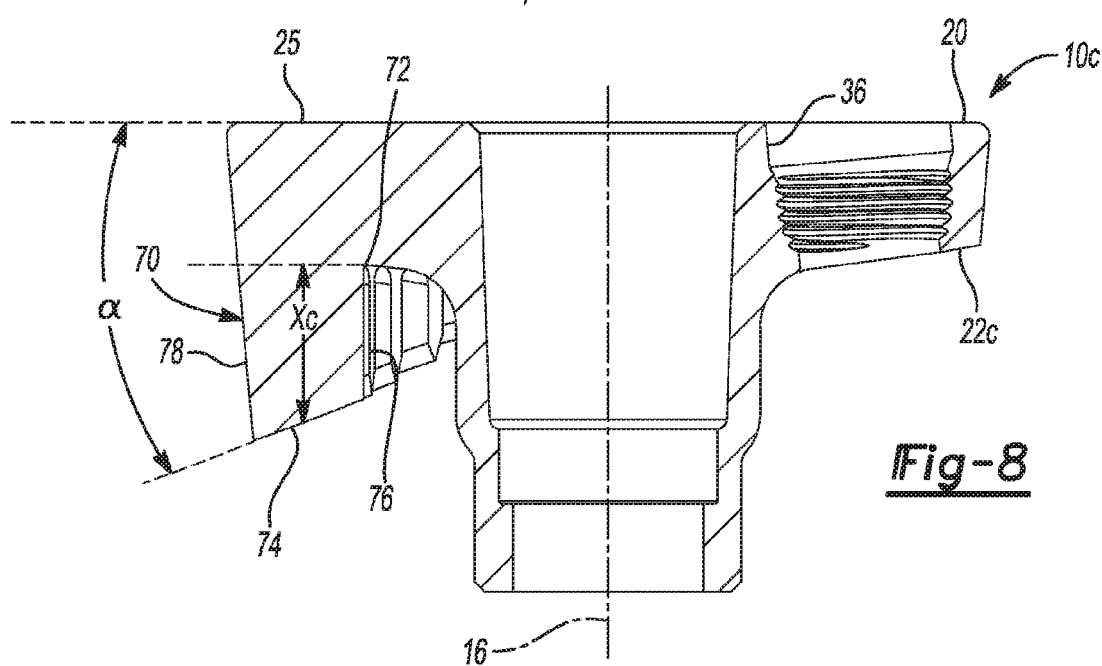
FIG. 8 is a cross-sectional view of the glenoid implant of FIG. 7, taken through the line 8-8.

With reference to FIGS. 6 through 8, another implant in accordance with the present teachings is illustrated and generally identified at reference character 10c. The structure and function of the implant 10c may be similar or identical to the structure and function of the implant 10 described above, apart from any exceptions described below and/or shown in the figures. Accordingly, similar features will not be described again in detail. Like reference numerals are used hereinafter and in the drawings to identify like components, while like reference numerals containing letter extensions (i.e., "c") are used to identify those components that have been modified.

The bone-engaging side 22c of the implant 10c may include a surface 26c. A plurality of bone-engaging blades or projections 70, separated by voids 71, may extend from the surface 26c. The projections 70 may extend from and between a proximal end 72 and a distal end 74 in a direction substantially parallel to the longitudinal axis 16. The projections 70 may further extend from and between a radially inner side 76 and a radially outer side 78 in a direction substantially perpendicular to the longitudinal axis 16. In this regard, the proximal end 72 may be adjacent and integral to the surface 26c, while the outer side 78 may be aligned with the peripheral surface 18c. As illustrated in FIG. 7, the inner side 76 and the stem 14 may define a radially extending void or gap 80 therebetween.

The distal end 74 of the projection 70 may define the angle α with the outer peripheral edge 25 of the articular side 20, such that the peripheral edge 25 and the distal ends 74 of the projections 70 define a substantially wedge-shaped construct, as illustrated in FIG. 8. In addition, as illustrated in FIGS. 6 and 8, a distance Xc between the proximal and distal ends 72, 74 may vary between consecutive projections 70, such that the distal ends 74 of consecutive projections 70 may define a convex profile. In some configurations, the distance Xc may also vary between the inner and outer sides 76, 78, such that the distal ends 74 define a substantially spherical profile.

As illustrated in FIG. 7, the plurality of projections 70 may extend about the longitudinal axis by an angle θc. In one configuration, the angle θc may be substantially equal to one hundred fifty degrees (150°). It will be appreciated, however, that the angle θ1 c may be greater or less than one hundred fifty degrees (150°) within the scope of the present disclosure. It will also be appreciated that, while the projections 70 are illustrated as having a blade-like construct, the projections 70 may have other configurations (e.g., spikes, stems, detents, etc.) within the scope of the present disclosure.

An example method of repairing a scapula with the implant 10c may include drilling or otherwise forming at least one hole in the scapula. A first hole can be sized for receiving the stem 14. A plurality of second holes can be sized for receiving the fasteners 38. A surface of the scapula can be reamed, or otherwise resurfaced, to remove an eroded portion of the bone. The implant 10c may be placed within the glenoid cavity such that the projections 70 are substantially aligned with the reamed or resurfaced portion of the bone. In this regard, the implant 10c may be rotated about the longitudinal axis 16 before the bone-engaging side 22c is engaged with the bone, such that the angle α formed by projections 70 allows the outer peripheral edge 25 of the articular side 20 to be substantially aligned, or otherwise flush with, the surface of the bone. Bone grafts may be placed in the voids 71 and the gap 80 to help ensure a secure fit between the implant 10c and the scapula. In addition, the surface 26c may include a porous coating to help ensure a secure fit between the implant 10c and the scapula. Thereafter, a force may be applied to the implant 10c in a direction substantially parallel to the axis 16 such that the projections 70 engage the scapula.

Figure 9A:
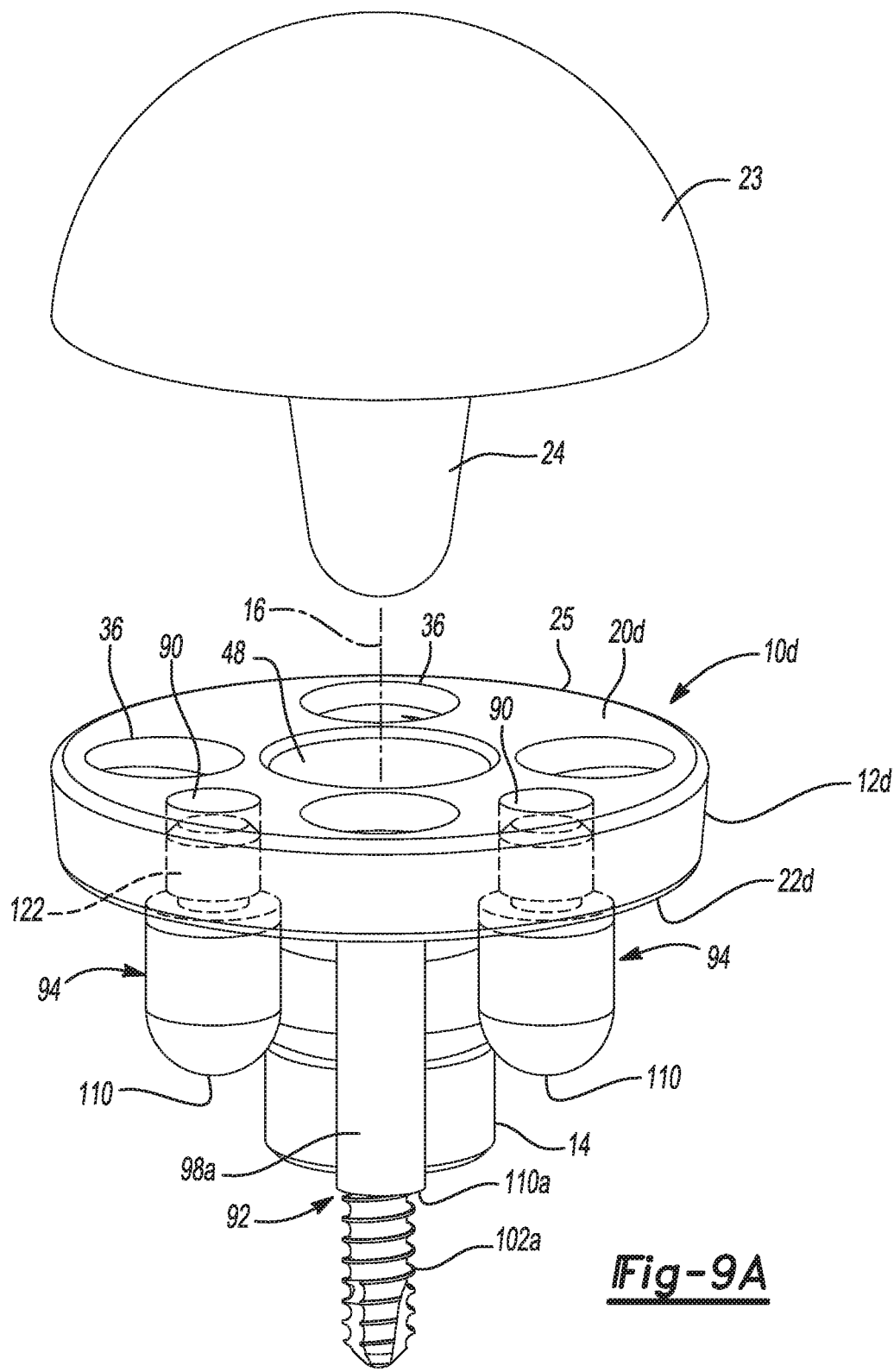
FIG. 9A is a perspective view of another glenoid implant constructed in accordance with the principles of the present disclosure, the glenoid implant including a first and second peg assemblies.

With reference to FIG. 9A, another in accordance with the present teachings is illustrated and generally identified at reference character 10d. The structure and function of the implant 10d may be similar or identical to the structure and function of the implant 10 described above, apart from any exceptions described below and/or shown in the figures. Accordingly, similar features will not be described again in detail. Like reference numerals are used hereinafter and in the drawings to identify like components, while like reference numerals containing letter extensions (i.e., "d") are used to identify those components that have been modified.

A second plurality of apertures 90 may extend through the body 12d, between the articular side 20d and the bone-engaging side 22d. As illustrated, in one configuration the implant 10d may include two equally sized and spaced apertures 90. It will be appreciated, however, that the implant 10 may include more or less than two apertures 90 within the scope of the present disclosure. Each aperture 90 may be located between adjacent apertures 36. In some configurations, the apertures 90 may extend through the body 12d in a direction substantially parallel to the longitudinal axis 16 and substantially perpendicular to the outer peripheral edge 25 of the articular side 20d. It will also be appreciated that the apertures 90 may extend through the body 12d at a non-parallel angle relative to the longitudinal axis 16 within the scope of the present disclosure.

The aperture 90 and/or the aperture 36 may be sized and shaped to receive a first peg assembly 92 and/or a second peg assembly 94. As illustrated in FIG. 10A, the first peg assembly 92 may include a peg member 96 and a housing 98. The peg member 96 may include a head portion 100 and a stem portion 102. The head portion 100 may include a threaded portion 104, such that the head portion 100 can be threadably received within the aperture 36 and/or the aperture 90. The stem portion 102 may include a substantially cylindrical construct. As illustrated in FIG. 9A, in one configuration a stem portion 102a may include a threaded portion 106 for threadably engaging the glenoid or other bone.

Figure 9B:
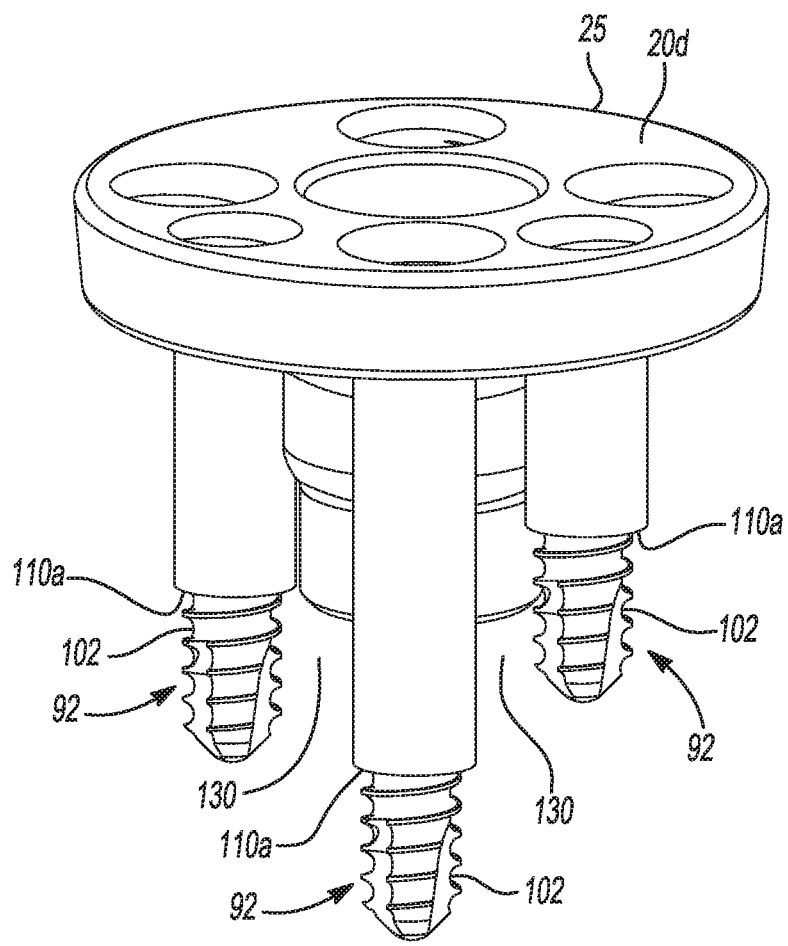
FIG. 9B is a perspective view of the glenoid implant of FIG. 9A including another peg assembly constructed in accordance with the principles of the present disclosure.

With reference to FIG. 10A, in one configuration the housing 98 may define a substantially cylindrical construct, including a first end 108 and a second end 110. In some configurations, the second end 110 may be a closed end. In this regard, the second end 110 may be rounded, or otherwise radiused, to minimize and disburse the transmission of forces and stresses between the housing 98 and the bone, as will be explained in more detail below. As illustrated in FIG. 9B, in other configurations a second end 110a of a housing 98a may be an open end. The housings 98, 98a may define a length L1 extending from the first end 108 to the second end 110, 110a, respectively. A cannulation 114 may extend between the first end 108 and the second end 110, 110a. As will be explained in more detail below, in an assembled configuration, the stem portion 102 of the peg member 92 may be disposed within the cannulation 114, such that the head portion 100 abuts the first end 108 of the housing 98.

As illustrated in FIG. 10B, the second peg assembly 94 may include a peg member 118 and the housing 98 or 98a. The peg member 118 may include a head portion 122, a stem portion 124 and a flange portion 126. The flange portion 126 may extend radially outward from the stem portion 124. In an assembled configuration, the stem portion 124 may be disposed within the housing 98 or 98a such that the flange portion 126 abuts the first end 108 of the housing.

As illustrated in FIGS. 9A and 9B, the length L1 of the housings 98, 98A may vary. Accordingly, the implant 10d may include any number of first and/or second peg assemblies 92, 94, each having a different length L1, such that in an assembled configuration a distance between the articular side 20d and the second ends 110 of the housings 98, 98a varies. In this regard, the the second ends 110 and the articular side 20d and/or the peripheral edge 25 may define a wedge-shaped construct. The head portions 100, 122 may be received by, or otherwise secured within, the aperture 90 or the aperture 36.

An example method of repairing a scapula with the implant 10d may include drilling or otherwise forming a plurality of holes in the scapula. A first hole can be sized for receiving the stem 14. A plurality of second holes can be sized for receiving the housings 98 and/or 98a. In this regard, based on the type and length L1 of the housing 98, 98a being used, the surgeon can drill the second holes to a predetermined length. The housings 98, 98a may be placed within the plurality of second holes. A diameter of the housings 98, 98a may be slightly greater than a diameter of the second holes, such that the housings 98, 98a interfere with, or are otherwise press-fit into, the second holes.

The implant 10d may be placed within the glenoid cavity such that the bone-engaging side 22d engages the scapula. The peg members 96, 118 may be placed within the apertures 36, 90 and the cannulation 114 to secure the implant 10d to the glenoid. In this regard, a diameter of the stem portion 102, 124 may be slightly greater than a diameter of the cannulation 114, such that the stem portions 102, 124 interfere with, or are otherwise press-fit into, the cannulation 114. As illustrated in FIG. 9B, in some configurations, the stem portions 102 may extend through the second end 110 of the housing 98 such that the stem portion 102 can extend into the glenoid to further secure the implant 10d relative to the glenoid. Bone grafts may be placed in gaps 130 between the body 12d and the peg assemblies 92, 94 to help ensure a secure fit between the implant 10d and the scapula.

Figure 11:
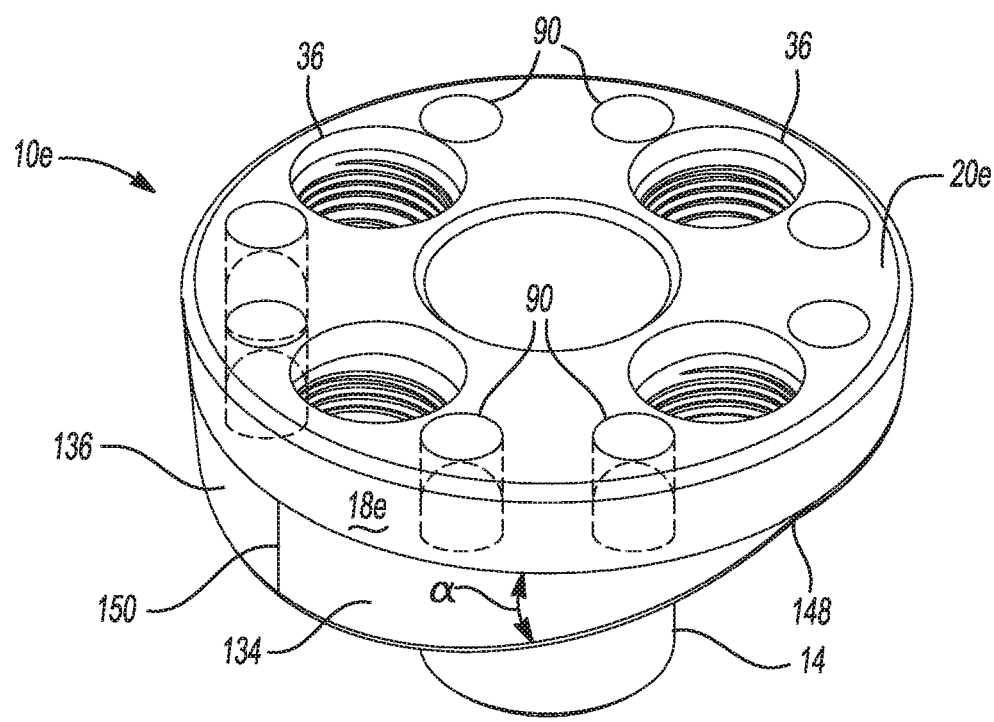
FIG. 11 is a perspective view of another glenoid implant constructed in accordance with the principles of the present disclosure, the glenoid implant including an insert.

With reference to FIGS. 11 through 128, another implant in accordance with the present teachings is illustrated and generally identified at reference character 10e. The structure and function of the implant 10e may be similar or identical to the structure and function of the implant 10d described above, apart from any exceptions described below and/or shown in the figures. Accordingly, similar features will not be described again in detail. Like reference numerals are used hereinafter and in the drawings to identify like components, while like reference numerals containing letter extensions (i.e., "e") are used to identify those components that have been modified.

Figure 12:
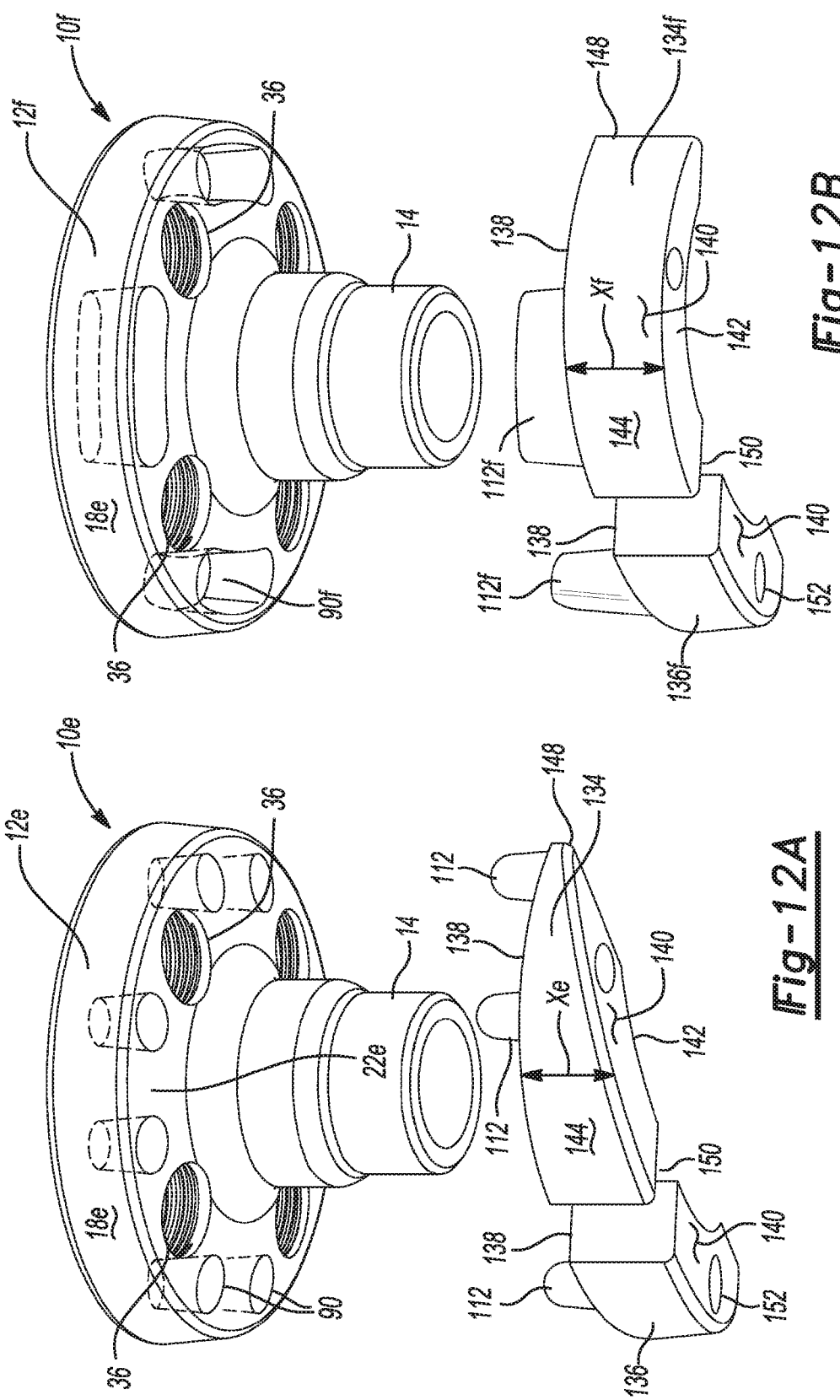
FIG. 12A is an exploded view of the glenoid implant of FIG. 11.
FIG. 12B is an exploded view of another glenoid implant constructed in accordance with the principles of the present disclosure.

The implant 10e may include a plurality of apertures 90 located between adjacent apertures 36. In some configurations, the apertures 90 may include a substantially circular cross sectional area (FIGS. 11 and 12A). It will be appreciated, however, that the apertures 90 may include other cross-sectional shapes within the scope of the present disclosure. For example, as illustrated in FIG. 12B, in some configurations, the apertures 90f may include an elongate or kidney-shaped cross section.

As illustrated, in one configuration, the implant 10e may include two apertures 90 located between each pair of adjacent apertures 36. In this regard, the apertures 90 may substantially define a circular pattern. The apertures 90, 90f may be tapered (e.g., a Morse taper) between the articular side 20e and the bone-engaging side 22e, such that a cross-sectional area of the aperture increases from the articular side to the bone-engaging side.

The implant 10e may further include a first insert 134 and a second insert 136. The first insert 134 may include an implant engaging surface 138, a bone-engaging surface 140, a radially inner surface 142, and a radially outer surface 144. The implant engaging surface 138 and the bone-engaging surface 140 define a distance Xe extending therebetween. In some configurations, the distance Xe may vary between the implant engaging surface 138 and the bone-engaging surface 140, such that the first insert 134 substantially defines a wedge-shaped construct (FIG. 12A). In other configurations, the distance Xe may be constant (FIG. 12B). Accordingly, in some configurations, a first insert 134f may define a substantially rectangular cross section.

The implant engaging surface 138 may include at least one peg 112. In some configurations, the implant engaging surface 138 may include two pegs 112. The peg 112 may be tapered (e.g., a Morse taper) such that a cross-sectional area of the peg 112 corresponds to the cross-sectional area of the aperture 90 to allow for a press-fit engagement between the peg 112 and the aperture 90. In this regard, in some configurations, the peg 112 may include a substantially circular cross sectional area (FIGS. 11 and 12A). It will be appreciated, however, that the peg 112 may include other cross-sectional shapes to correspond with the shape of the aperture 90. For example, as illustrated in FIG. 12B, in some configurations, the peg 112f may include an elongate or kidney-shaped cross section to correspond with the shape of the aperture 90f.

The radially inner surface 142 may extend arcuately from and between first and second ends 148, 150 of the first insert 134. In this regard, the radially inner surface 142 may be concave. The radially outer surface 144 may oppose the radially inner surface 142 and extend arcuately from and between the first and second ends 148, 150. In this regard, the radially outer surface 144 may be convex.

The second insert 136 may be similar or identical to the structure and function of the first insert 134 described above, apart from any exceptions described below and/or shown in the figures. Accordingly, similar features will not be described again in detail. Like reference numerals are used hereinafter and in the drawings to identify like components. The second insert 136 may include an aperture 152 extending between the implant engaging surface 138 and the bone-engaging surface 140. In some configurations, the aperture 152 may be disposed between consecutive pegs 112.

As illustrated in FIGS. 12A and 12B, in an assembled configuration, the body 12 and the first and second inserts 134, 136 define a substantially wedge-shaped implant 10e. The pegs 112, 112f may be disposed in the apertures 90, 90f such that the peripheral surface 18e of the body 12e is substantially aligned or flush with the radially outer surface 144 of the first and second inserts 134, 136. In this regard, the first end 148 of the first implant 134, 134f, and the second end 150 of the second implant 136, 136f can define an angle $\theta g$ extending about the axis 16.

Figure 13:
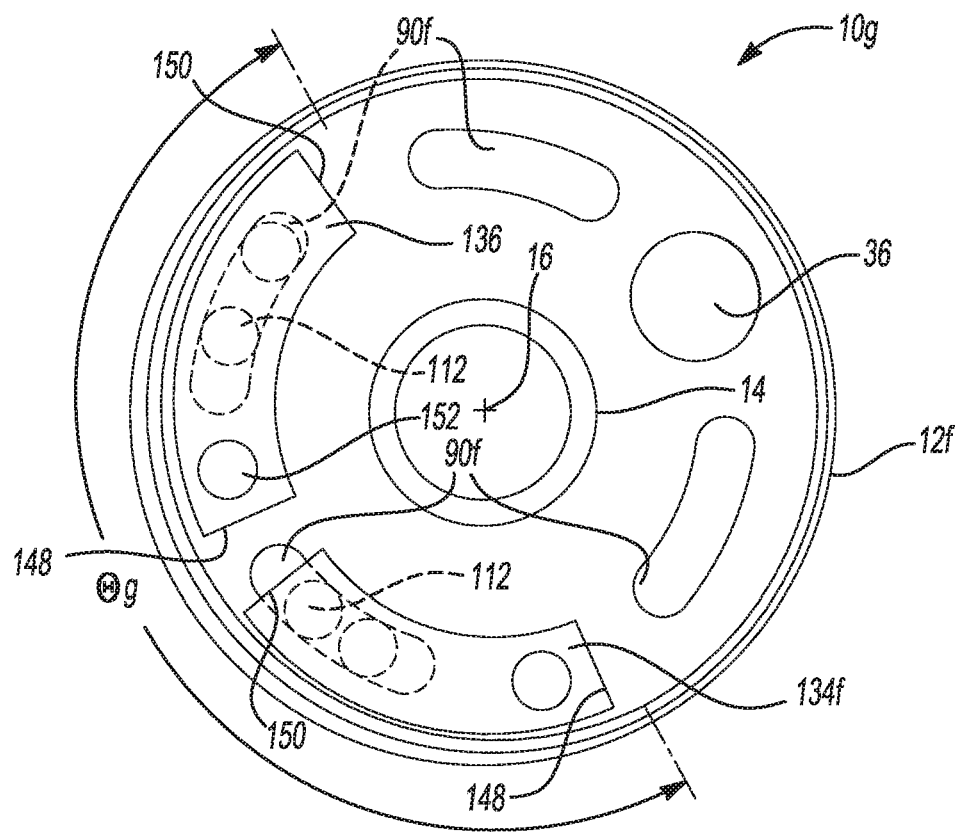
FIG. 13 is a bottom view of another glenoid implant constructed in accordance with the principles of the present disclosure.

As illustrated in FIG. 13, in some configurations of an implant 10g, the pegs 112 of the first and/or second insert 134, 136 can be inserted into the apertures 90f of the body 12f. Similarly, the insert 134f can include the pegs 112. Inserting the substantially cylindrical pegs 112 into the elongate or substantially kidney-shaped apertures 90f, can allow the first inserts 134, 134f and/or the second inserts 136, 136f to rotate relative to the body 12f, such that the angle θg is adjustable. In this regard, the pegs 112 may be slidably, or otherwise movably disposed in the apertures 90f. Rotating the first insert 134, 134f and/or the second insert 136, 136f relative to the body 12f can allow the implant 10g, including the inserts 134, 134f, 136, 136f, to cover a larger deficiency or eroded portion of the bone.

It will be appreciated that the augmented or wedge-shaped construct of the implants 10, 10a, 10b, 10c, 10d, 10e, 10f and 10g can improve the surgical implantation of the implants by accounting for erosion and wear patterns in the bone. Accounting for erosion and wear patterns in the bone can help to minimize or eliminate the need for bone grafts and excessive reaming of the bone, thereby reducing the amount of surgical time, while ensuring the accurate and secure placement of the implant relative to the bone.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terms "approximately," "generally," "about," and "substantially," as used to describe particular angles, shall be understood to encompass the stated angle and a range of one to two degrees (1°-2°).

The invention claimed is:

1. A glenoid implant, comprising:
   a body portion that includes an articular side and a concave bone-engaging side opposite the articular side;
   a stem portion extending from the bone-engaging side of the body portion along a longitudinal axis;
   a plurality of peripheral pegs configured to extend parallel to one another from the bone-engaging side of the body portion; and
   a plurality of teeth extending from the bone-engaging side of the body portion, the teeth being formed as indentations on a concave base surface of the concave bone-engaging side, the concave base surface being spaced farthest away from an outer peripheral edge of the articular side at a first location, the first location defining a first axis extending from the first location through the longitudinal axis such that the first axis is orthogonal to the longitudinal axis, the first location further defining a second axis extending through an intersection of the first axis and the longitudinal axis such that the second axis is orthogonal to both the first axis and the longitudinal axis, the indentations being deepest along the second axis with decreasing depth away from the second axis.

2. The glenoid implant of claim 1, wherein each peripheral peg includes a cylindrical body that is configured to extend from a proximal end, adjacent to the bone-engaging side of the body portion, to a distal end, away from the bone-engaging side of the body portion.

3. The glenoid implant of claim 2, wherein each peripheral peg includes at least one annular groove formed in a peripheral surface of the cylindrical body of the peripheral peg.

4. The glenoid implant of claim 3, wherein:
   a proximal portion of the cylindrical body has a body diameter; and
   the annular groove forms a waist that has a waist diameter around the cylindrical body, the waist diameter being less than the body diameter.

5. The glenoid implant of claim 2, wherein each peripheral peg includes a plurality of annular grooves formed in a peripheral surface of the cylindrical body of the peripheral peg.

6. The glenoid implant of claim 5, wherein in a cross-section taken parallel to the peripheral peg, each annular groove has a cross-section that is concave and smoothly varying from a proximal end of the annular groove to a distal end of the annular groove.

7. The glenoid implant of claim 5, wherein each peripheral peg includes an annular fin portion formed in the peripheral surface of the cylindrical body of the peripheral peg and positioned adjacent one of the annular grooves.

8. The glenoid implant of claim 7, wherein:
   a proximal portion of the cylindrical body has a body diameter; and
   the annular fin portion has a fin diameter around the cylindrical body, the fin portion diameter being greater than the body diameter.

9. The glenoid implant of claim 8, wherein in a cross-section taken perpendicular to the peripheral peg, the annular fin portion has a circular cross-section having a fin diameter that remains constant from a proximal end of the annular fin portion to a distal end of the annular fin portion.

10. The glenoid implant of claim 8, wherein the annular fin portion is shaped to deform or flex upon forming a press-fit connection.

11. The glenoid implant of claim 5, wherein each peripheral peg includes a plurality of annular fin portions formed in the peripheral surface of the cylindrical body of the peripheral peg and positioned such that each adjacent pair of annular fin portions surround an annular groove.

12. The glenoid implant of claim 5, wherein each peripheral peg includes:
   three annular fin portions formed in the peripheral surface of the cylindrical body of the peripheral peg; and
   two annular grooves formed in the peripheral surface of the cylindrical body of the peripheral peg and interspersed with the three annular fin portions.

13. A method for repairing a shoulder joint using a glenoid implant, the method comprising:
   drilling a first hole in a scapula of the shoulder joint, the first hole being sized to receive a stem of the glenoid implant;
   drilling a plurality of second holes parallel to one another in the scapula, each of the second holes being sized to receive a respective peripheral peg of the glenoid implant;
   shaping a surface of the scapula to remove an eroded portion of bone;
   placing the glenoid implant within a glenoid cavity of the shoulder joint, such that a concave base surface of a bone-engaging side of the glenoid implant aligns with the shaped surface of the scapula and the peripheral pegs of the glenoid implant align with the plurality of second holes in the scapula, the bone-engaging side including a plurality of teeth extending from the bone-engaging side of the body portion, the teeth being formed as indentations on a concave base surface of the concave bone-engaging side, the concave base surface being spaced farthest away from an outer peripheral edge of the articular side of the glenoid implant, opposite the bone-engaging side, at a first location, the first location defining a first axis extending from the first location through the longitudinal axis such that the first axis is orthogonal to the longitudinal axis, the first location further defining a second axis extending through an intersection of the first axis and the longitudinal axis such that the second axis is orthogonal to both the first axis and the longitudinal axis, the indentations being deepest along the second axis with decreasing depth away from the second axis;
   forcing the glenoid implant against the scapula such that annular fins on the peripheral pegs of the glenoid implant form a press-fit against the second holes in the scapula;
   inserting bone cement into the second holes in the scapula; and
   flowing the bone cement into annular grooves formed between adjacent annular fins on the peripheral pegs of the glenoid implant.

14. The method of claim 13, further comprising, before placing the glenoid implant:
   rotating the glenoid implant about a longitudinal axis of the stem of the glenoid implant to align an outer peripheral edge of an articular side of the glenoid implant with a surface of the bone.

15. A glenoid implant, comprising:
   a body portion that includes an articular side and a concave bone-engaging side opposite the articular side;

a stem portion extending from the bone-engaging side of the body portion along a longitudinal axis;

a plurality of peripheral pegs configured to extend parallel to one another from the bone-engaging side of the body portion, each peripheral peg including:

a cylindrical body that is configured to extend from a proximal end, adjacent to the bone-engaging side of the body portion, to a distal end, away from the bone-engaging side of the body portion, a proximal portion of the cylindrical body having a body diameter;

an annular groove formed in a peripheral surface of the cylindrical body of the peripheral peg, the annular groove forming a waist that has a waist diameter around the cylindrical body, the waist diameter being less than the body diameter; and an annular fin portion formed in the peripheral surface of the cylindrical body of the peripheral peg and positioned adjacent one of the annular grooves, the annular fin portion having a fin diameter around the cylindrical body, the fin diameter being greater than the body diameter; and a plurality of teeth extending from the bone-engaging side of the body portion, the teeth being formed as indentations on a concave base surface of the concave bone-engaging side, the concave base surface being spaced farthest away from an outer peripheral edge of the articular side at a first location, the first location defining a first axis extending from the first location through the longitudinal axis such that the first axis is orthogonal to the longitudinal axis, the first location further defining a second axis extending through an intersection of the first axis and the longitudinal axis such that the second axis is orthogonal to both the first axis and the longitudinal axis, the indentations being deepest along the second axis with decreasing depth away from the second axis.

16. The glenoid implant of claim 15, wherein:

in a cross-section taken parallel to the peripheral peg, the annular groove has a cross-section that is concave and smoothly varying from a proximal end of the annular groove to a distal end of the annular groove; and in a cross-section taken perpendicular to the peripheral peg, the annular fin portion has a circular cross-section having a fin diameter that remains constant from a proximal end of the annular fin portion to a distal end of the annular fin portion, the fin diameter being greater than the body diameter.

17. The glenoid implant of claim 15, wherein the annular fin portion is shaped to deform or flex upon forming a press-fit connection.

* * * * *